(12) United States Patent
Welker

(10) Patent No.: US 6,764,536 B2
(45) Date of Patent: Jul. 20, 2004

(54) SAMPLING DEVICE WITH LIQUID ELIMINATOR

(75) Inventor: Brian H. Welker, Sugar Land, TX (US)

(73) Assignee: Welker Engineering Company, Sugar Land, TX (US)

( * ) Notice: Subject to any disclaimer, the term of this patent is extended or adjusted under 35 U.S.C. 154(b) by 8 days.

(21) Appl. No.: 10/302,055

(22) Filed: Nov. 22, 2002

(65) Prior Publication Data

US 2004/0099143 A1 May 27, 2004

(51) Int. Cl.$^7$ ............................................. B01D 19/00
(52) U.S. Cl. ........................ 96/189; 96/413; 55/417; 55/420; 55/503; 73/863.23
(58) Field of Search .................. 96/189, 413; 55/417, 55/420, 503; 73/863.12, 863.21, 863.23

(56) References Cited

U.S. PATENT DOCUMENTS 6,357,304 B1 * 3/2002 Mayeaux ................. 73/863.23

OTHER PUBLICATIONS

*Welker Sampling Accessories*; Welker Engineering Company Product Distribution Catalog; 2001; 2 pgs.; Sugar Land, Texas, US.
*Welker Liquid Eliminator Filter Regulator*; Welker Engineering Company Product Distribution Catalog; 2001; 1 pg.; Sugar Land, Texas, US.
*Welker Probe Style Instrument Regulator*; Welker Engineering Company Product Distribution Catalog; 2001; 2 pgs.; Sugar Land, Texas, US.
*Welker F–23 Low Pressure Filter Dryer*; Welker Engineering Company Product Distribution Catalog; 2001; 1 pg.; Sugar Land, Texas, US.
*Welker Instrument Air Dehydration Assembly*; Welker Engineering Company Product Distribution Catalog; 2001; 1 pg.; Sugar Land, Texas, US.
Genie Probe Regulator; Genie Product Distribution; A+ Corporation; 1999; Prairieville, Louisiana USA.
Genie GPRi Probe Regulator; Genie Product Distribution; A+ Corporation; 2001; Prairieville, Louisiana USA.
Liquid Eliminator; A+ Corporation; 2001; 2 pgs.; Prairieville, Louisiana USA.

* cited by examiner

Primary Examiner—Robert A. Hopkins
(74) Attorney, Agent, or Firm—Blackwell Sanders Peper Martin LLP

(57) ABSTRACT

An integrated sampling device with liquid eliminator is provided. The device includes a body with integrated valving. A liquid eliminator device is provided within the body and interposed in a flow path such that gas will pass through and liquid will not. The gas will then be conducted to a sampling device while the liquid will pass through an exhaust port back to the source of fluid. An inlet valve is also provided to control the flow of fluid from the source to the liquid eliminator element. An outlet valve may be provided to control liquid back to the source.

18 Claims, 6 Drawing Sheets

SAMPLING DEVICE WITH LIQUID ELIMINATOR

BACKGROUND OF INVENTION

In the natural gas industry, samples of the natural gas product are frequently extracted from a source for testing such things as the constituents and Btu value of the natural gas. Natural gas, even though generally referred to as gas, when being transported, may contain both liquid and gas hydrocarbon components. Oftentimes, a monitoring instrument such as a gas chromatograph is mounted on or connected to a conduit transporting the natural gas. It is desired to separate the liquid component from the gaseous component because many instruments will not accept the liquid component and still function properly. As seen in FIG. 1, an exemplary prior art device for connecting a sampling instrument to the conduit is illustrated and the parts are identified therein. The prior art apparatus includes various connectors, tubing and valves connecting a body with a liquid eliminator to a pipeline or other natural gas source. The body includes a cap and a base connected together. A sample is extracted through an intake and conducted through various connectors and other plumbing devices including a separate but attached inlet valve that is operable for selectively permitting flow into an inlet of the body. The sample transfers from the body inlet to a chamber and to a liquid separator such as a porous membrane backed by a support screen. The gaseous component transfers from the chamber to an instrument through the separator. The membrane allows gaseous components to pass through but not liquid components. The separated liquid is collected in the chamber and exhausted through a body outlet through various plumbing devices such as an outlet valve, connectors, tubing and flare fittings as well as an exhaust for discharge back into the conduit.

As can be seen, the prior art liquid eliminator and plumbing is complex, provides many joints each with a potential for leaking and requires separate valves. While the prior art liquid eliminators are somewhat effective, they do pose the above problems. A prior art liquid eliminator of the type shown in FIG. 1 is a model LE-2 from Welker Engineering of Sugar Land, Tex. In addition to the aforementioned problems, prior art liquid eliminators utilize relatively expensive valves which are separate from the liquid eliminator and attached thereto through various connectors and plumbing devices. Typically, such valves are made of stainless steel. An example of such a valve is a model NV-1 from Welker Engineering.

In view of the problems with the prior art devices, there is a need for a liquid eliminator apparatus that allows the integration of the various components and the elimination of many of the plumbing components to provide a simplified and more reliable liquid eliminator.

The present invention provides such an integrated structure.

SUMMARY OF INVENTION

The present invention provides for a liquid eliminator usable with a sampling device for extracting samples from a source of natural gas. The device includes a body with an inlet and first and second outlets. A connector portion on the body in one form is adapted for connecting the body directly to a fitting portion of a conduit, e.g., a pipeline or the like in which natural gas is contained. The body has a flow passage connecting the inlet in flow communication with the first and second outlets. First and second shut off valve assemblies are mounted in the body with the first valve assembly cooperating with the flow passage downstream of the inlet and upstream of the first and second outlets and is operable to selectively permit and prevent flow from the inlet to the first and second outlets. The second valve assembly cooperates with the flow passage upstream of the second outlet and is operable to selectively permit and prevent flow into and out of the second outlet. A separator is positioned, flow wise, between the first valve assembly and the first outlet. The separator is operable to separate liquid from a fluid in the flow passage preventing liquid from flowing out of the first outlet and for discharge from the body through the second outlet.

BRIEF DESCRIPTION OF DRAWINGS

FIG. 6 is a sectional view taken along the line 6—6, FIG. 5, to illustrate the positional details of the intake and outlet.

FIG. 7 is a sectional view of a liquid eliminator in combination with an extendable and retractable intake and outlet and shown mounted on a natural gas pipeline. The intake is shown in a retracted position.

Like numbers throughout the various Figures of the drawings designate like or similar parts.

DETAILED DESCRIPTION

Figure 1:
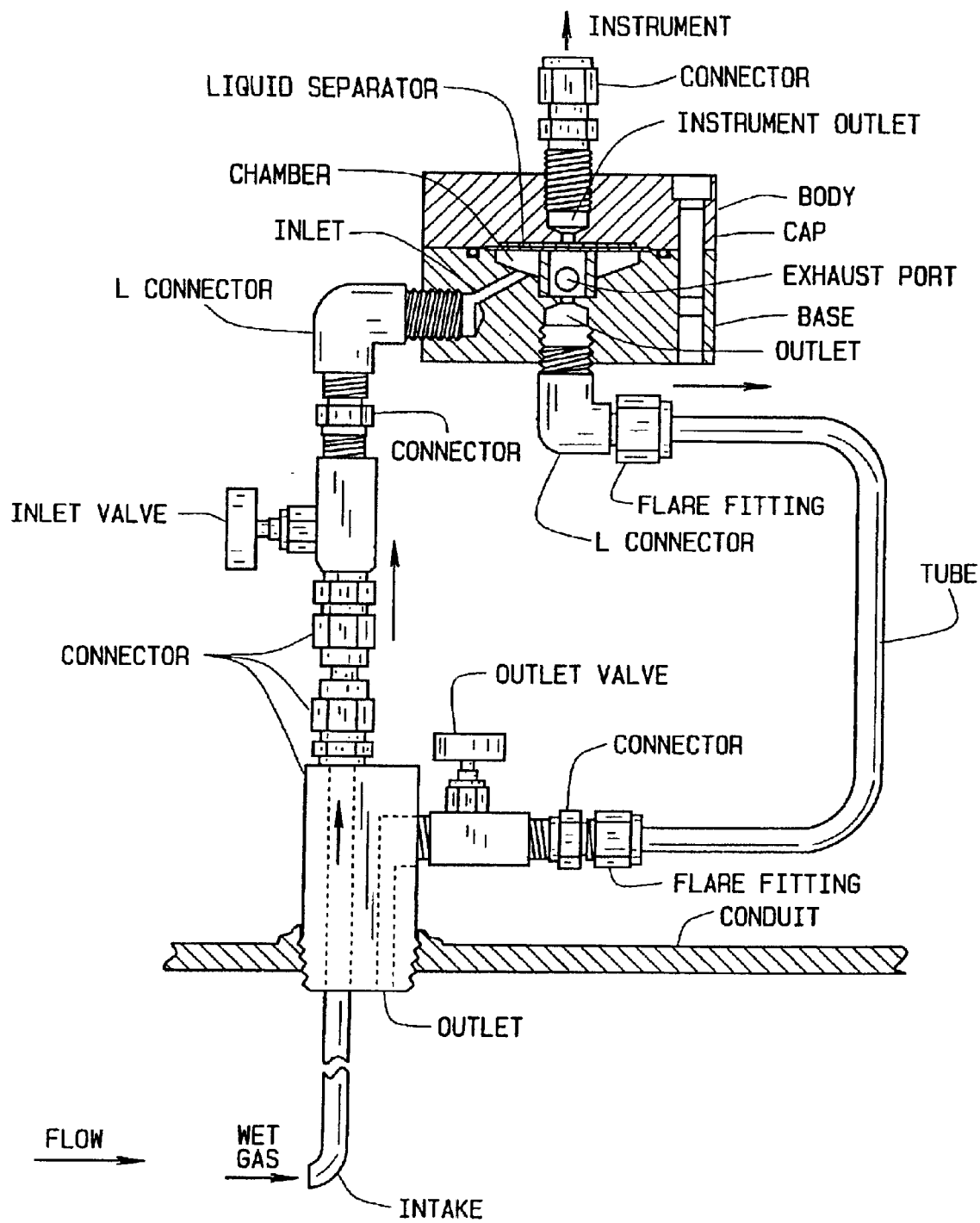
FIG. 1 is a partial sectional view of a prior art liquid eliminator usable with a sampling device.
Figure 2:
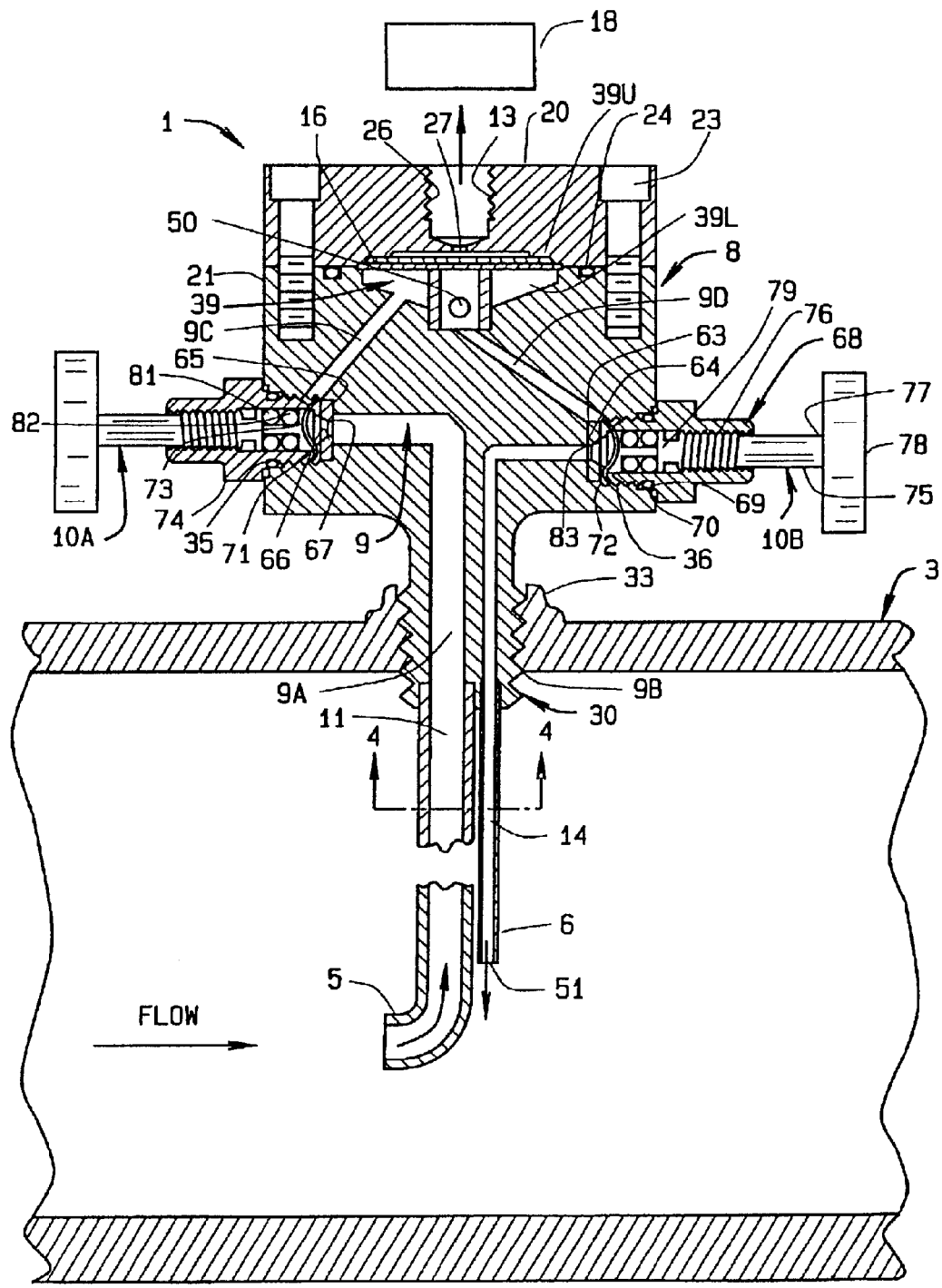
FIG. 2 is a sectional view of a liquid eliminator of the invention shown in combination with a natural gas pipeline with a pitot tube type intake.
Figure 3:
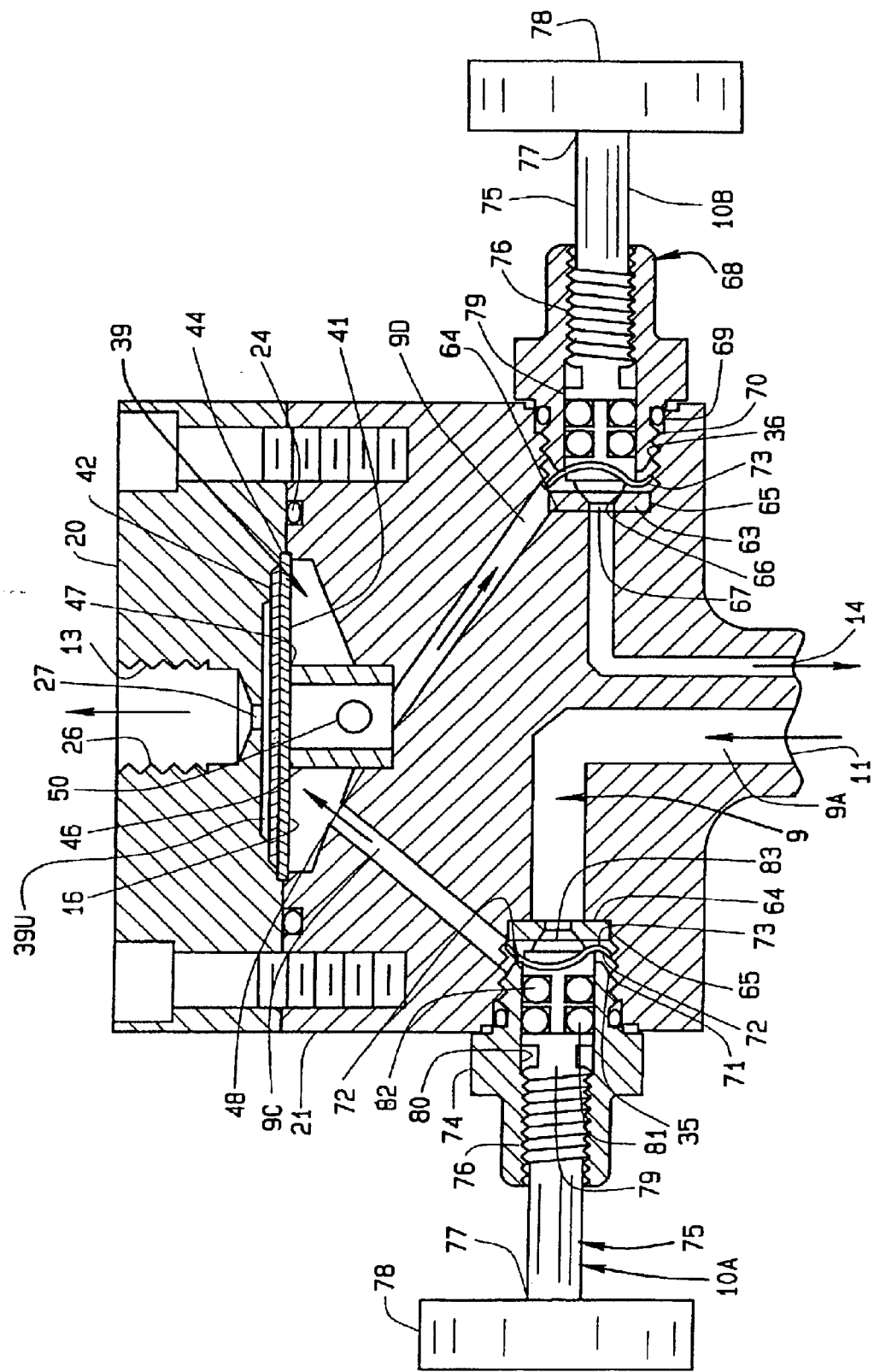
FIG. 3 is an enlarged fragmentary sectional view of a liquid eliminator similar to that shown in FIG. 2.
Figure 4:
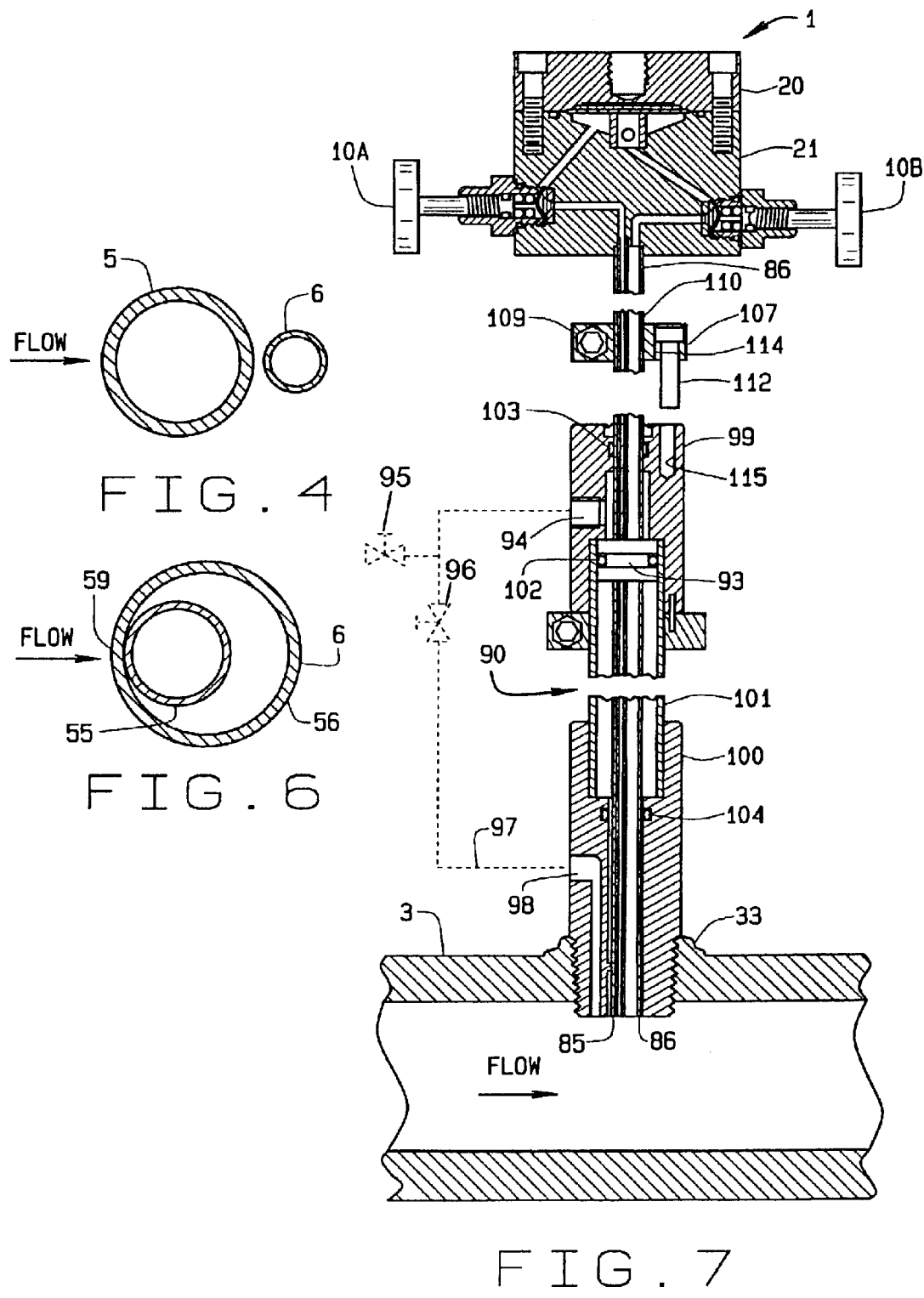
FIG. 4 is a sectional view taken along the line 4—4, FIG. 2, to illustrate positional details of the intake and outlet.

As best seen in FIGS. 2 and 3, the liquid eliminator sampling device designated generally 1 is mounted to a source 3 of fluids such as a conduit or pipeline transporting natural gas. The device 1 includes an intake 5, at least one valve designated generally 10 (two being shown as 10A 10B) an exhaust 6, a body designated generally 8 with a flow passage 9 forming a communication path between an inlet 11 and first and second outlets 13, 14 respectively. A separator 16 is positioned, flow wise, between the inlet 11 and the outlet 13 and is operable to separate liquid components of the natural gas from the gaseous components with the liquid component being dischargable through the outlet 14 while at least some of the gaseous component is dischargable through the outlet 13. The outlet 14 and inlet 11 are in direct flow communication, i.e., the separator is not in between flow wise. At least one valve 10 is provided in the body 8 for controlling flow of fluid from the source 3 to the outlet 13. A sampling device shown schematically as 18, such as a gas chromatograph, is connected to the outlet 13 for receipt of a sample therefrom.

The body 8 includes a cap 20 removably secured to a base 21 as by socket head cap screws 23. The cap 20 is sealed to the base 21 by a suitable seal member 24 such as an O-ring. Preferably the cap 20 and base 21 have a generally round transverse cross sectional shape and are made of a durable material such as metal alloy. In the form of the invention shown, the outlet 13 is formed in the cap 20 and includes a threaded portion 26 having a through bore 27 at the bottom thereof for communicating with the passage 9 for directing fluid to the sampling device 18. A coupler, not shown, is used to connect the sampling device 18 in flow communication with the passageway 9.

The base 21 includes a coupler designated generally 30, preferably integral therewith, for securement to the source 3. As shown, the coupler 30 is an externally threaded nipple that is adapted for threaded and sealing engagement with an internally threaded coupler 33 which is secured to the source 3. An acceptable coupler 33 is a Thread-o-let® coupler that is secured to the source 3, as for example by welding. The threads of the couplers 30 and 33 may be a pipe thread for interference sealing engagement or may be straight threads, and a sealing agent such as sealing tape or pipe sealer may be used. This connection can be a flange connection as is known in the art. In addition, a separate sealing element as for example an O-ring may be used to seal the coupler 30 to the coupler 33. In the use of the device as shown, there is only one separable joint between the base 21 and the source 3. The flow passage 9 includes two branches 9A and 9B. The flow passage 9 also includes valve ports 35, 36 each adapted for the attachment of a respective valve assembly 10 which are designated for differentiation as 10A for the inlet valve assembly and 10B for the outlet valve assembly. A passage branch 9C communicates between the valve port 35 and a chamber 39 portion of the flow passage 9. The inlet valve assembly 10A is positioned flow wise downstream of the intake 5 and inlet 11 and upstream of the chamber 39 and outlet 13. The chamber 39 is comprised of a lower portion 39L formed in the base 21 and an upper portion 39U formed in the cap 20. A passage branch 9D communicates between the chamber 39 and the valve port 36. The outlet 14 communicates with the valve port 36 for discharge of fluid through the exhaust 6. Thus, the flow passage 9 is operable for directing flow of fluid from the intake 5 to the exhaust 6 by flowing through the inlet 11, the branches 9A, 9B, 9C, 9D, valve ports 35, 36, outlet 14 to the exhaust 6 for discharge back into the source 3. The passage branches 9A-D may be formed as for example by drilling and the valve ports 35, 36 may also be formed by drilling and tapping and are adapted for mounting the valves assemblies 10A, 10B therein.

The separator 16 is positioned flow wise downstream of the valve port 35 and upstream of the outlet 13. As shown, the separator 16 is positioned in the chamber 39 and can be retained in place by being gripped between the cap 20 and base 21. Preferably, the separator 16 includes porous membrane 41 that has pores sized to allow the gas to flow therethrough from the chamber lower portion 39L into the chamber upper portion 39U and then to the outlet 13. Such porous membranes are well known in the art and the control of fluid flow therethrough is through control of the pore size. The pores form gas flow channels through the membrane 41. For strength and durability, the porous membrane 41 is secured to a backing 42 such as a metal screen which is positioned preferably on the downstream side (top side as seen in FIG. 2), flow wise, of the separator 16. Preferably, the separator 16 has portions positioned in a recess 44 which can be formed in either or both of the cap 20 and base 21.

Both the passage branches 9C and 9D open into the lower portion 39L of the chamber 39. A threaded insert 46 is positioned in the lower portion 39L and is in the form of a tubular member having an upper end 47 positioned for engagement with the separator 16 and a lower end 48 secured to the base 21 as by mutual threaded engagement. The insert 46 provides for support of the separator 16 while providing a flow path for liquid collected in the chamber 39 to be discharged therefrom through a port 50 in the side wall of the insert 46.

One form of the invention is illustrated in FIG. 2. It utilizes as an intake member 5, a pitot tube style intake, having an inlet end facing upstream into the direction of flow of fluid in the source 3 which can be a natural gas pipeline or the like. The exhaust 6 is physically positioned on a downstream side of the intake 5 which helps provide a reduced pressure at an outlet end 51 because of the flow of the fluid around the intake 5. As shown, in FIG. 2, the exhaust 6 is a straight tubular member secured to the base 21 as by press fitting, welding, silver soldering, or threaded engagement at the free end of the coupler 30. Likewise, the intake 5 can be a separate part from the base 21 and can be press fit, welding, silver soldering or threaded in the coupler 30. As shown, the outlet end 51 is also positioned closer to the coupler 30 than is the free end of intake 5.

The valve assemblies, 10A, 10B are similar in construction. The valve assemblies 10 each include a valve seat 63 in a respective port 35, 36. The seat 63 is preferably as a separate part resting on a bottom wall 64 within a cylindrical portion 65 of the respective valve port. The valve seat 63 may be made of a polymeric material such as PTFE and preferably has a tapered seat surface 66 with a flow opening 67 in line with the respective passage branch 9A, 9B to permit flow of fluid therethrough. In addition to the valve seat 63, the valve assemblies 10 also include a valve body designated generally 68 threaded into respective port 35, 36 and sealed to the base 21 as with an O-ring 69 contained in a groove 70 and engaging a sealing surface at the respective port 35, 36. The valve body 68 has a threaded section 71 in sealing threaded engagement with the threaded portion of the respective port 35, 36 and is attached directly to the base 21. The base 21 functions as a valve housing for the valve assembly and valve body. The threaded section 71 of the valve body 68 has a free end 72. A wave disc spring 73 is positioned between the free end 72 and the respective valve seat 63 resiliently holding the valve seat 63 in engagement with the bottom wall 64 by controlling the spacing between the wall 64 and end 72. The valve body 68 includes a hex head 74 to facilitate installation and tightening of the valve body into the base 21. The valve body 68 is provided with a generally cylindrical internal threaded portion for removably and moveably mounting a valve stem 75 within the valve body 68. The valve stem 75 includes a threaded shank 76 having a free end 77 on which a handle 78 can be mounted. Preferably the handle 78 is removably mounted on the shank 76. The valve stem 75 includes a generally cylindrical seal carrying portion 79 having mounted therein one or more seal members 81 such as O-rings, each in a respective groove 82. The seal carrying portion 79 is received in a cylindrical portion 80 of the valve body 68 with the seal members 81 forming a seal between the valve stem 75 and the valve body 68. The valve stem 75 has a valve element closure portion 83 sized and shaped to cooperate with the valve seat 63 and the seat surface 66 to effect sealing engagement there between. When sealed, flow through the passage 9 is prevented in and out. Although the valve seats 63 are each shown as a separate part, it is to be understood that the valve seat may be formed directly in the material of the base 21, if desired, thus eliminating the need for the springs 73.

Figure 5:
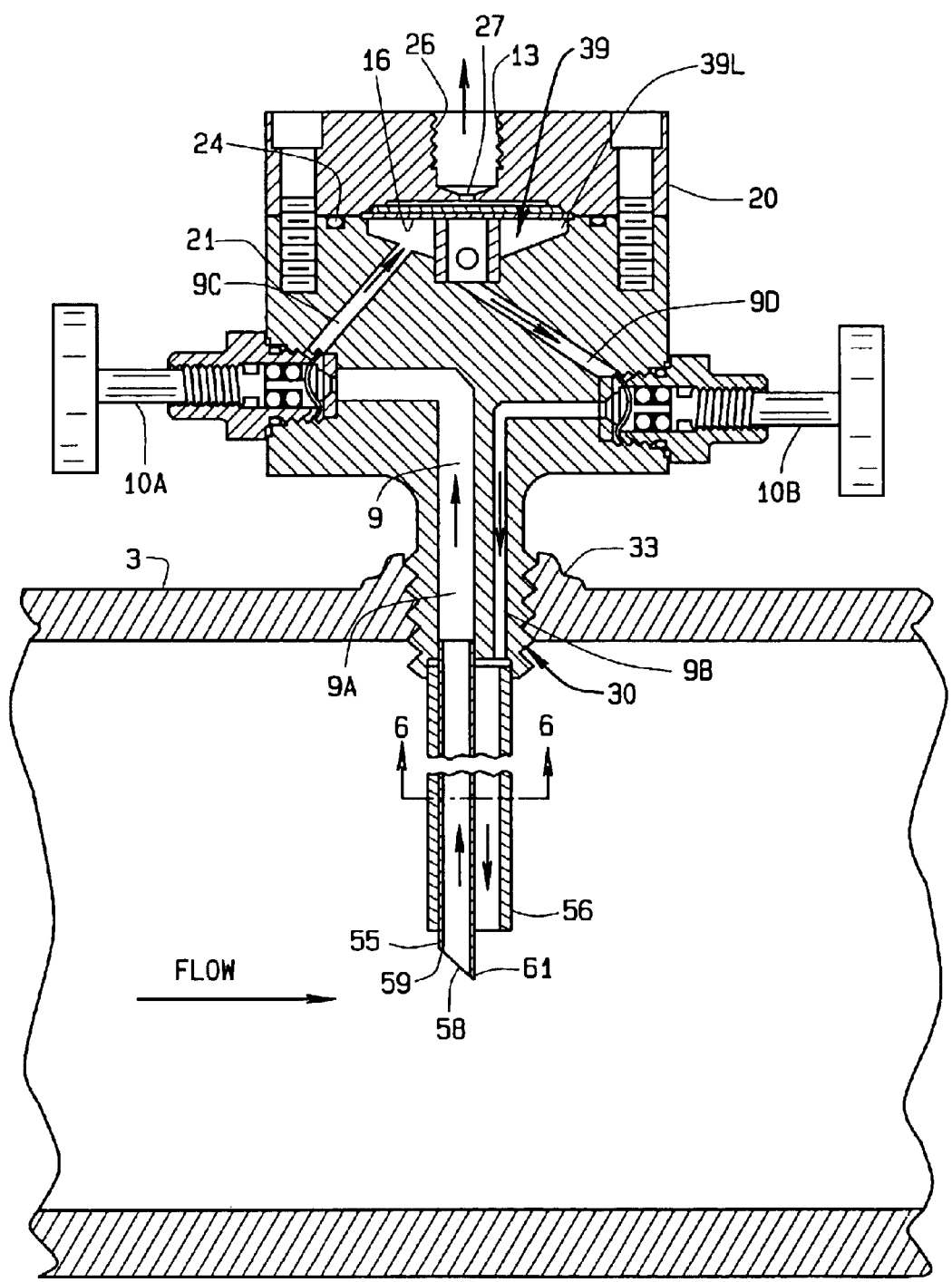
FIG. 5 is a sectional view of a liquid eliminator similar to that shown in FIG. 2 but using a different arrangement for the intake and outlet.

A second embodiment of the invention is shown in FIGS. 5,6. It is similar to the construction of the embodiment shown in FIG. 2 with the exception of the intake and exhaust arrangement. As seen in FIGS. 5, 6, an intake 55 is positioned internally of an exhaust 56. Preferably the intake 55 is positioned on the upstream side of the exhaust 56 to help create a negative pressure on the backside thereof as fluid flows thereby to help induce flow of fluid through the flow passage 9. Further, the intake 55 has a beveled end 58 which inclines downwardly and rearwardly from a leading edge 59 toward a trailing edge 61. The intake 55 and exhaust 56 are shown in cross sectional plan view in FIG. 6 to illustrate their relative orientations. The remainder of the device 1 of FIG. 5 is as shown and described for the form shown in FIG. 2.

Figure 8:
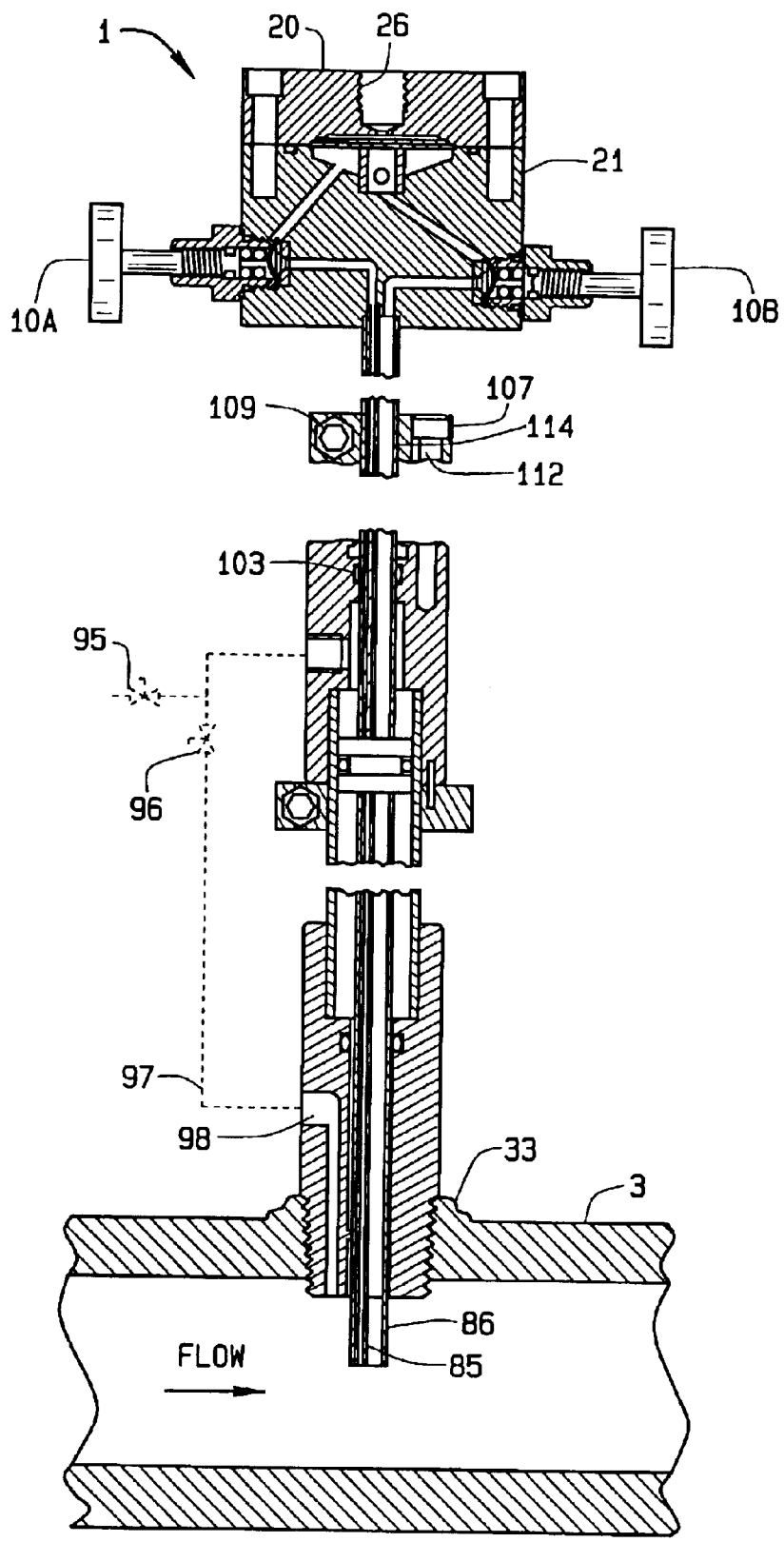
FIG. 8 is a liquid eliminator as shown in FIG. 7 but showing the intake in an extended position in the natural gas pipeline.

FIGS. 2–6 illustrate a device 1 in two embodiments that have their respective intakes and exhausts for example intake 5 or 55 and exhaust 6 or 56 in fixed relationship to the source 3. FIGS. 7, 8 illustrate an another alternative embodiment of the present invention. FIG. 7 shows an intake 85 and exhaust or discharge 86 retracted and FIG. 8 shows the intake 85 and exhaust 86 extended. The intake 85 and exhaust 86 are tubes and are similar in construction and relative positions as for the form of the inventions shown in FIG. 3.

Mechanism is provided for selectively moving the intake 85 and exhaust 86. However it is to be understood that the mechanism could also be provided to selectively move the intake 85 and exhaust 86 independently or only the intake 85. In the form of the invention shown in FIG. 7 and FIG. 8, the device 1 is substantially the same as that shown in FIGS. 2, 3 and 5 with regard to the body 8 and valves 10 and are therefore not redescribed herein. A housing 90 is provided and has an interior chamber 91. The housing 90 forms a cylinder for receipt of a moveable piston 93 that operates for extension under the influence of pressurized fluid from the source 3 received through a port 94. Flow of fluid from the source 3 to the port 94 is controlled by a control valve 96 connected in a pressure fluid line 97 that connects to an intake port 98 that in turn opens into the interior of the source 3. Exhaust of pressurized fluid from the housing 90 is effected via exhaust valve 95 also connected in the line 97. Exhausting the fluid from the housing 90 allows retraction of the piston 93 under influence of the pressurized fluid in the source 3. The pressurized fluid from the source 3 is the principal or majority and preferably the sole external source of energy to move the intake 85 and exhaust 86 between their extended and retracted positions. The housing 90 is comprised of a head 99 and base 100 connected together by a tubular member 101 in which the piston 93 is moveably mounted. The intake 85 and exhaust 86 are elongate hollow tubes and are mounted on the piston 93 for movement therewith simultaneously. A seal 102 seals the piston to the interior wall of the cylinder 101, a seal 103 seals the exhaust 86 to the head 99 and a seal 104 seals the exhaust 86 to the base 100. The exhaust 86 and intake 85 are secured to the piston 93 as by threaded engagement, welding, silver soldering or press fitting therewith in a sealed manner. The exhaust 86 and intake 85 communicate with the passageway 9 as described above for the embodiments of the invention shown in FIGS. 2–5.

When the piston 93 moves, the body 8 moves therewith both when the intake 85 is inserted into the source 3 or retracted therefrom. To secure the intake 85 and exhaust 86 in their extended position, a lock collar 107 which is mounted on the exterior of the exhaust 86 may be clamped in a desired position thereon as with a socket head cap screw 109 which will permit expansion and retraction of a hole 110 through the collar 107. A fastening device 112 such as a hex head cap screw extends through a countersunk bore 114 for receipt in a threaded bore 115. When the intake 85 and exhaust 86 are in their extended position, the collar 107 will move into proximity with the head 99 so that the fastener 112 can be threaded into the threaded bore 115 to secure the collar 107 and hence the piston 93, intake 85 and exhaust 86 in their extended positions. When it is desired to retract the intake 85 and exhaust 86 the fastener 112 may be removed from threaded engagement with the bore 115 and the pressure relieved on the backside of the piston 93 which will allow pressurized fluid from the source 3 to apply force to the exhaust 86 to move the piston 93 to its retracted position as well as the intake 85 and exhaust 86. Pressure on the piston 93 or the exhaust 86 may be used to retain the intake 85 and exhaust 86 in their extended or retracted positions respectively.

Thus, there has been shown and described several embodiments of a novel invention. As is evident from the foregoing description, certain aspects of the present invention are not limited by the particular details of the examples illustrated herein and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An integrated sampling device with liquid eliminator, said device is adapted for connection to a conduit for directing a sample of fluid in the conduit to a sampler, said device including:

a body with an inlet and first and second outlets, said body having a connector portion adapted for connection directly to a coupler portion of a conduit;

a flow passage contained in the body connecting the inlet in flow communication with the first and second outlets;

first and second shut off valves mounted in the body with the first valve cooperating with the flow passage downstream of the inlet and upstream of the first and second outlets and operable to selectively permit and prevent flow from the inlet to the first and second outlets, said second valve cooperating with the flow passage upstream of the second outlet and operable to selectively permit and prevent flow into and out of the second outlet; and a separation device positioned, flow wise, between the first valve and the first outlet and operable to separate liquid from gas in the fluid in the flow passage preventing liquid from flowing out of the first outlet and for discharge from the body through the second outlet.

2. A device as forth in claim 1 wherein the first and second valves each include a valve seat positioned in the body and a valve element, each valve element is moveably mounted to the body and selectively movable into and out of engagement with a respective said valve seat.

3. A device as set forth in claim 2 wherein the valve seats are removably mounted in the body.

4. A device as set forth in claim 2 wherein the valve elements are threadably mounted in the body whereby rotation of the valve element moves a seal portion of the valve element into or out of engagement with a respective said valve seat.

5. A device as set forth in claim 1 wherein the separation device includes a porous element with flow channels communicating between opposite sides thereof with the channels being operable to allow gas to flow therethrough for flow of gas from the inlet to the first outlet and restricting flow of liquid through the channels to the first outlet.

6. A device as set forth in claim 5 wherein the flow passage includes a chamber, said porous element separating said chamber into a first portion and a second portion, said inlet and second outlet communicate directly with the first chamber portion and the first outlet communicates directly with the second chamber portion, the first chamber portion is adapted to collect liquid separated from the gas by the porous element.

7. A device as set forth in claim 6 wherein the second outlet is in direct flow communication with the first chamber portion for discharge of liquid collected in the first chamber portion through the second outlet.

8. An integrated sampling device with liquid eliminator, said device includes:
    a body with an inlet and first and second outlets, said body having a connector portion adapted for connection directly to a fitting portion of a pipe adapted to carry flow of hydrocarbon fluid;
    said inlet including an intake member adapted to extend into a portion of the interior of the conduit when the body is mounted on the pipe;
    a flow passage internal to the body connecting the intake and first and second outlets in flow communication;
    first and second shutoff valves mounted in the body with the first valve cooperating with the flow passage downstream of the intake and upstream of the first and second outlets and operable to selectively permit and prevent flow from the intake to the first and second outlets, said second valve cooperating with the flow passage upstream of the second outlet and operable to selectively permit and prevent flow in and out of the second outlet; and
    a separation device positioned, flow wise, between the first valve and the first outlet and operable to separate liquid from the hydrocarbon fluid flowing through the flow passage preventing liquid from flowing out of the first outlet and for discharge from the body through the second outlet.

9. A device as set forth in claim 8, wherein said second outlet includes an exhaust member adapted to extend into the interior of the pipe when the body is mounted on the pipe.

10. A device as set forth in claim 8 wherein the intake member includes a pitot tube.

11. A device as set forth in claim 8 wherein the intake member includes a tube.

12. A device as set forth in claim 11 wherein the tube has a beveled free end.

13. A device as set forth in claim 9 wherein the intake member is positioned outside of the exhaust member.

14. A device as set forth in claim 9 wherein at least a portion of the intake member is positioned inside a portion of the exhaust member.

15. An integrated sampling device with liquid eliminator, said device adapted for connection to a conduit for directing a sample of fluid in the conduit to a sampler, said device including:
    a housing including a body and a cover secured to the body said body having an interior flow passage with a chamber, an inlet, an outlet and a discharge, said flow passage connecting the inlet, outlet and discharge in flow communication;
    first and second shut off valves each having a valve body valve element and valve seat mounted to the body and each having a handle exterior of the body, said body forming a valve housing for each of the first and second valves the first valve cooperates with the flow passage flow wise downstream of the inlet and upstream of the outlet and the second valve cooperates with the flow passage flow downstream of the inlet and upstream of the discharge, said first and second valves are operable to selectively permit and prevent flow of fluid therethrough; and
    a separation device mounted in said chamber and positioned, flow wise, between the first valve and the outlet and between the second valve and the outlet, said separation device is operable to separate liquid from the fluid in the flow passage preventing liquid from flowing out of the outlet.

16. A device as set forth in claim 15 wherein the cover is removably secured to the body whereby removal of the cover provides access to the separation device.

17. A device as set forth in claim 16 wherein the inlet includes an intake and the device further includes a drive operably connected to the intake and discharge and operable connectable to move the intake and discharge between extended and retracted positions and being operably connectable to the conduit to provide pressurized fluid from the conduit thereto to move the intake and discharge to at least one of the extended and retracted positions.

18. A device as set forth in claim 17 wherein the drive is operable to utilize the pressurized fluid as an external principal source of drive energy to move the intake and discharge.

* * * * *